(12) United States Patent
Levorse, Jr. et al.

(10) Patent No.: US 6,632,788 B2
(45) Date of Patent: Oct. 14, 2003

(54) POLYALKYLBICYLIC DERIVATIVES

(75) Inventors: Anthony T. Levorse, Jr., So. Amboy, NJ (US); Anubhav P.S. Narula, Hazlet, NJ (US); Edward Mark Arruda, Cliffwood, NJ (US); Charles E.J. Beck, Summit, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 266 days.

(21) Appl. No.: 09/859,953

(22) Filed: May 17, 2001

(65) Prior Publication Data

US 2003/0004090 A1 Jan. 2, 2003

(51) Int. Cl.$^7$ ................................................. A61K 7/46
(52) U.S. Cl. .................. 512/14; 512/8; 512/9; 512/11; 512/13; 512/15; 512/16; 512/17; 512/22; 512/23; 512/25; 512/26; 549/200; 549/330; 549/331; 549/356; 549/381; 549/385; 568/300; 568/303; 568/376; 568/377; 568/379
(58) Field of Search .................. 512/8, 9, 11, 13, 512/14, 15, 16, 17, 22, 23, 25, 26; 549/200, 330, 331, 356, 381, 385; 568/300, 303, 376, 377, 379

(56) References Cited

U.S. PATENT DOCUMENTS

| | | |
|---|---|---|
| 3,847,993 A | 11/1974 | Hall et al. |
| 3,927,083 A | 12/1975 | Hall et al. |
| 4,534,891 A | 8/1985 | Boden et al. |
| 5,227,367 A | 7/1993 | Boden et al. |
| 5,665,698 A | 9/1997 | Narula et al. |
| 5,733,866 A | 3/1998 | Narula et al. |

FOREIGN PATENT DOCUMENTS

| | | |
|---|---|---|
| DE | 2330648 | 1/1974 |
| EP | 0 395 199 A1 | 10/1990 |
| EP | 0 825 166 A2 | 2/1998 |
| JP | 09249584 | 9/1997 |

Primary Examiner—Jill Warden
Assistant Examiner—Monique T. Cole
(74) Attorney, Agent, or Firm—Joseph F. Leightner

(57) ABSTRACT

The compound according to the formula set forth below

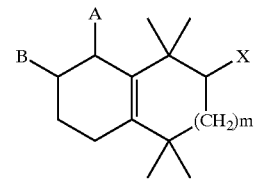

where A is

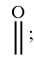

B is

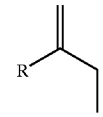

or A and B together form the ring structure

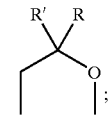

and X, R' and R are independently H and $CH_3$ and m=0 or 1.

and the use of the compound in creating fragrances, and scents in items such as perfumes, colognes and personal care products is disclosed.

17 Claims, No Drawings

POLYALKYLBICYLIC DERIVATIVES

FIELD OF THE INVENTION

The present invention relates to new chemical entities and the incorporation and use of the new chemical entities as fragrance chemicals.

BACKGROUND OF THE INVENTION

U.S. Pat. Nos. 5,227,367; 5,733,866; and 5,665,698 hereby incorporated by reference as iset forth in their entirety disclose polycyclic chemicals that are suitable for use as fragrance chemicals. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds, represented by the structure of Formula I set forth below:

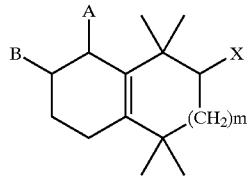

where A is

B is

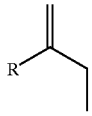

or A and B together form the ring structure

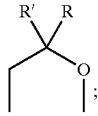

and X, R' and R are independently H and $CH_3$ and m=0 or 1.

Another embodiment of the invention is a method for enhancing a fragrance by incorporating an olfactory acceptable amount of the compound provided above.

These and other embodiments of the present invention will be apparent by reading the following specification.

DETAILED DESCRIPTION OF THE INVENTION

The novel compounds of the present invention are more fully described by the following structures:

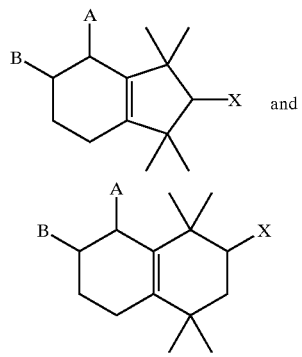

where X, A, and B are as described above.

Those with skill in the art will appreciate that the dotted line represents a single or double bond. In a preferred embodiment the molecule does not contain a double bond. In a highly preferred embodiment the molecules contain the ring structure without the double bond and m=0. These molecules are represented by the following structure:

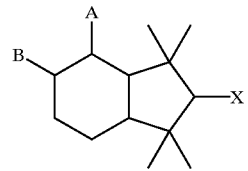

where A, B and X have the definition set forth above. In a preferred embodiment of the invention the compounds have the following structure

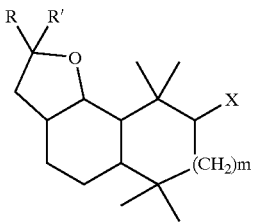

Most preferably M=0 and R and R' are independently selected from H and $CH_3$.

Highly preferred embodiments of the invention are the following compounds wherein the substituents have the following values when applied to the compound of Formula I:

| COMPOUND | A, B, X, M. VALUES | | | |
|---|---|---|---|---|
| 4,10,10,11,12,12-hexamethyl-3-oxatricyclo [7.3.0.0,<2,6>] dodecane | A and B together form the 5 member ring structure and R is H and R' is $CH_3$ | (intentionally left blank) | X is $CH_3$ | M = 0; and the rings are saturated |
| 4,4,10,10,11,12-12-heptamethyl-3-oxatricyclo [7.3.0.0,<2,6>] dodecane | A and B together form the 5 member ring structure and R is $CH_3$ and R' is $CH_3$ | (intentionally left blank) | X is $CH_3$ | M = 0; and the rings are saturated |
| 1,1,2,3,3-penta-methyl-5-prop-2-enyl-2,3,5,6,7- | A is = 0 | B is the ketone structure and R is H | X is $CH_3$ | M = 0; and the double |

-continued

| COMPOUND | A, B, X, M. VALUES | | | |
|---|---|---|---|---|
| pentahydroinden-4-one | | | | bond is present |
| 1,1,2,3,3-penta-methyl-5-(2-methylprop-2-enyl)-2,3,5,6,7-pentahydroinden-4-one | A is = O | B is the ketone structure and R is $CH_3$ | X is $CH_3$ | M = 0; and the double bond is present |

The novel compounds of the present invention are prepared by one of several reaction sequences set forth below. The compounds of Examples 1, 2, 3, 8, 9, 10, 12, 13, and 14, set forth below, were prepared by the sequence:

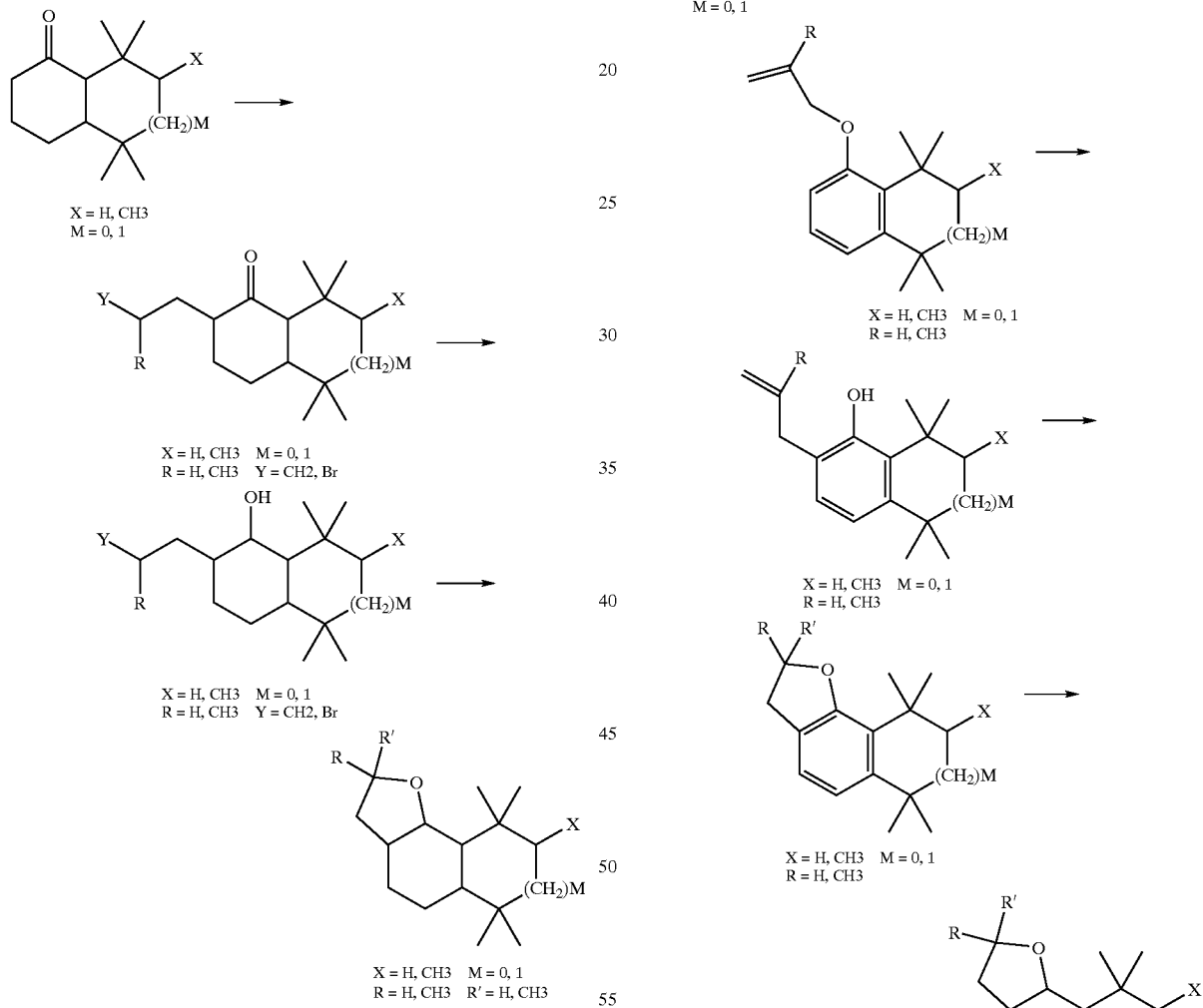

The reaction sequence set forth above is summarized by the following reactions. The first reaction is a three (3) carbon addition via allyl alcohol Claisen rearrangement or carbon alkylation with methallyl chloride. This reaction (Claisen rearrangement) is typically conducted at a temperature of from about 150 to about 250° C. In a preferred embodiment the reaction is catalyzed using an acid catalyst, preferably methanesulfonic acid or para toluenesulfonic acid. The carbon addition reaction is then followed by an aluminum hydride ketone reduction reaction. The ketone is reduced to form the corresponding alcohol. The final reaction set forth above is an acid catalyzed ether formation that is conducted at a temperature of from about 70 to about 130° C. This reaction is usually conducted in a solvent such as xylene or toluene with toluene being the preferred solvent.

The compounds of Examples 5–7 were prepared by the following general sequence:

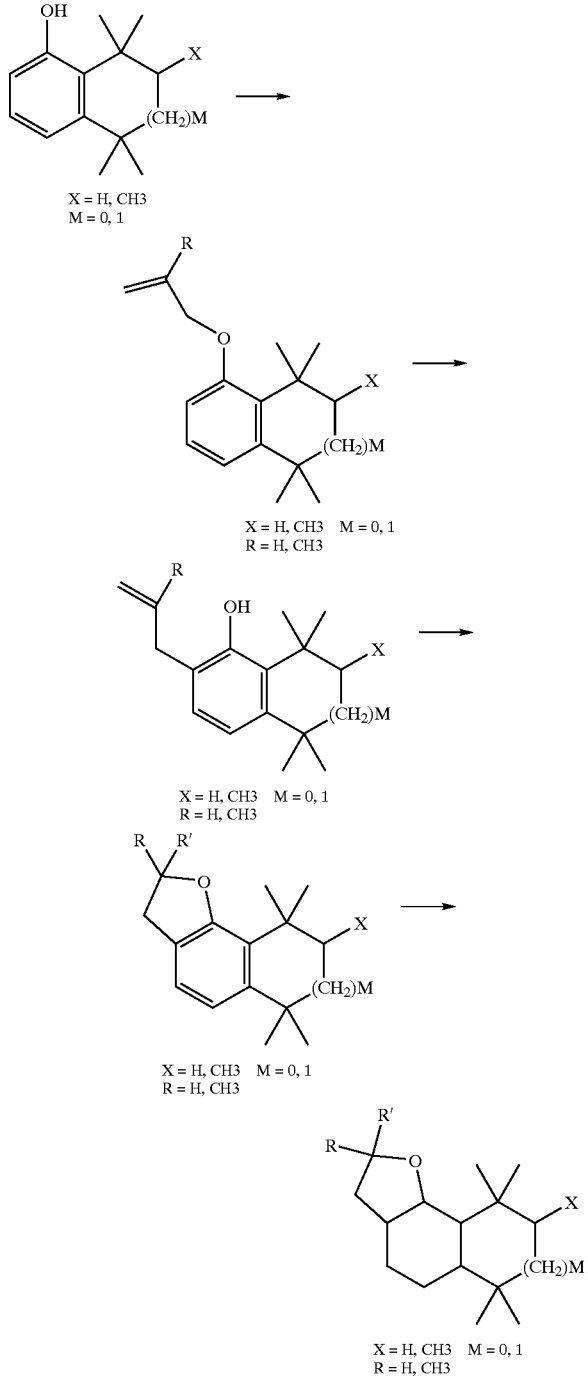

The first reaction is a carbon alkylation employing either allyl chloride or methallyl chloride depending if the desired R group is H or $CH_3$. This reaction is typically conducted at a temperature of from about 23 to about 100° C. The reaction is usually conducted with a base catalyst employing sodium methoxide or sodium hydroxide. The next reaction is a thermal Claisen rearrangement conducted at a temperature of from about 170 to about 250° C. The third reaction is an acid catalyzed ether formation employing similar temperatures and catalysts as described above, followed by a catalytic hydrogenation employing rhodium or platinum as a catalyst.

The compounds of Examples 4 and 11 are prepared by the sequence:

pounds. As used herein the compounds described herein include the isomeric mixtures of the compounds as well as those isomers that may be separated using techniques known to those with skill in the art. Suitable techniques include chromatography, particlularly gel chromatography.

The optical isomers for the compound 4,10,10,11,12,12-hexamethyl-3-oxatricyclo[7.3.0.0<2,6>]dodecane are provided in the following table. One with skill in the art would be able to formulate fragrance compositions using one or more or the following isomers and mixtures of the isomers:

| | | |
|---|---|---|
| (1R, 2R, 4R, 6R, 9R, 11R)-Z | (1S, 2S, 4R, 6R, 9S, 11S)-Z | (1S, 2R, 4R, 6R, 9S, 11S)-Z |
| (1R, 2R, 4R, 6R, 9R, 11S)-Z | (1R, 2S, 4R, 6S, 9R, 11S)-Z | (1R, 2R, 4R, 6S, 9S, 11S)-Z |
| (1R, 2R, 4R, 6R, 9S, 11R)-Z | (1S, 2S, 4S, 6R, 9S, 11R)-Z | (1S, 2R, 4R, 6R, 9R, 11S)-Z |
| (1R, 2R, 4R, 6S, 9R, 11R)-Z | (1S, 2S, 4R, 6S, 9R, 11S)-Z | (1S, 2S, 4S, 6S, 9S, 11S)-Z |
| (1R, 2R, 4S, 6R, 9R, 11R)-Z | (1S, 2R, 4S, 6R, 9S, 11S)-Z | (1S, 2R, 4S, 6S, 9R, 11S)-Z |
| (1R, 2S, 4R, 6R, 9R, 11R)-Z | (1R, 2S, 4R, 6S, 9S, 11S)-Z | (1S, 2S, 4R, 6R, 9R, 11S)-Z |
| (1S, 2R, 4R, 6R, 9R, 11R)-Z | (1S, 2S, 4R, 6R, 9S, 11R)-Z | (1S, 2S, 4S, 6R, 9R, 11R)-Z |
| (1R, 2R, 4R, 6R, 9S, 11S)-Z | (1S, 2R, 4R, 6S, 9S, 11R)-Z | (1S, 2S, 4R, 6S, 9S, 11R)-Z |
| (1R, 2R, 4R, 6S, 9S, 11R)-Z | (1S, 2R, 4R, 6S, 9R, 11S)-Z | (1R, 2R, 4S, 6S, 9S, 11S)-Z |
| (1R, 2R, 4S, 6S, 9R, 11R)-Z | (1R, 2R, 4S, 6R, 9S, 11S)-Z | (1S, 2R, 4S, 6R, 9S, 11S)-Z |
| (1R, 2S, 4S, 6R, 9R, 11R)-Z | (1R, 2R, 4S, 6S, 9R, 11S)-Z | (1S, 2S, 4S, 6R, 9R, 11S)-Z |
| (1S, 2S, 4R, 6R, 9R, 11R)-Z | (1R, 2S, 4R, 6R, 9S, 11R)-Z | (1S, 2S, 4R, 6R, 9S, 11R)-Z |
| (1R, 2R, 4R, 6S, 9S, 11S)-Z | (1R, 2S, 4R, 6S, 9R, 11R)-Z | (1S, 2R, 4R, 6S, 9S, 11S)-Z |
| (1R, 2R, 4S, 6S, 9S, 11R)-Z | (1R, 2R, 4S, 6R, 9R, 11S)-Z | (1S, 2S, 4R, 6R, 9S, 11S)-Z |
| (1R, 2S, 4S, 6S, 9R, 11R)-Z | (1R, 2S, 4R, 6R, 9S, 11S)-Z | (1S, 2S, 4S, 6R, 9R, 11S)-Z |
| (1S, 2S, 4S, 6R, 9R, 11R)-Z | (1R, 2R, 4S, 6S, 9R, 11R)-Z | (1S, 2S, 4S, 6S, 9R, 11S)-Z |
| (1R, 2S, 4S, 6S, 9S, 11R)-Z | (1S, 2R, 4S, 6R, 9S, 11R)-Z | (1R, 2S, 4S, 6S, 9S, 11S)-Z |
| (1R, 2R, 4R, 6S, 9R, 11S)-Z | (1S, 2S, 4S, 6S, 9S, 11R)-Z | (1S, 2S, 4R, 6S, 9R, 11S)-Z |
| (1R, 2R, 4S, 6R, 9S, 11R)-Z | (1S, 2S, 4S, 6S, 9R, 11S)-Z | (1R, 2S, 4S, 6R, 9S, 11R)-Z |
| (1R, 2S, 4R, 6S, 9R, 11R)-Z | (1S, 2S, 4S, 6R, 9S, 11S)-Z | (1R, 2S, 4S, 6R, 9R, 11S)-Z |
| (1S, 2R, 4S, 6R, 9R, 11R)-Z | (1S, 2S, 4R, 6S, 9S, 11S)-Z | (1S, 2R, 4S, 6S, 9S, 11S)-Z |
| (1R, 2R, 4S, 6S, 9R, 11S)-Z | | |

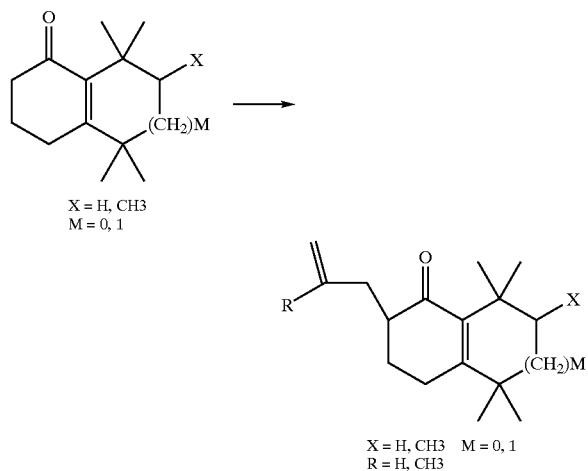

X = H, CH3
M = 0, 1

X = H, CH3   M = 0, 1
R = H, CH3 wherein the reaction is a three (3) carbon addition via allyl alcohol Claisan rearrangement or carbon alkylation with methallyl chloride using the conditions and catalysts described above.

The starting materials when M=0 for the above described reaction can be found in U.S. Pat. Nos. 5,227,367, 5,733,866 and 5,665,698. Similarly, the starting materials for the above materials when M=1 can be found in U.S. Pat. No. 3,927,083, hereby incorporated by reference, German patent 2330648 and Japanese patent 09249584.

Those with skill in the art will recognize that the compounds of the present invention have several chiral centers, thereby providing numerous isomers of the claimed com- The compounds of the present invention have a powerful amber fragrance, with soft, woody notes.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the fragranced article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to mean parts per million; mm is understood to be millimeters, ml is understood to be milliliters, Bp is understood to be boiling point, THF is understood to be tetrahydrofuran, Hg is understood to be mercury and g is understood to be grams. IFF as used in the examples is understood to mean International Flavors & Fragrances Inc., Hazlet, N.J., USA.

EXAMPLE 1

Preparation of 7,7,8,9,9-pentamethyl-3-prop-2-enylbicyclo [4.3.0]nonan-2-one

The synthesis of the starting material for this example is set forth in U.S. Pat. Nos. 5,227,367, 5,733,866, 5,665,698.

A 3 liter flask equipped with a vigreux column and a distillation head was charged with 624 g (3 mole) of 7,7,8,9,9-pentamethylbicyclo[4.3.0]nonan-2-one, 435 g (7.5 mole) allyl alcohol, 97 g (1.6 mole) acetic acid, and 15 g (0.16 mole) methanesulfonic acid. The mixture was heated to 80–85° C. Trimethyl orthoformate 350 g (3.3 mole) was added over 24 hours with removal of lights (methanol) atmospherically. The reaction mass was heated to 180° C. with removal of lights and aged at 180° C. for 2 hr. The crude reaction mass was cooled and 800 ml of water and 400 ml of toluene was added. The aqueous layer was discarded and the organic layer was washed with brine.

The crude organic layer was distilled to recover toluene as well as 285 g of 7,7,8,9,9-pentamethyl-3-prop-2-enylbicyclo [4.3.0]nonan-2-one as a mixture of isomers (Bp 106° C. at 1 mmHg).

The nmr spectrum of 7,7,8,9,9-pentamethyl-3-prop-2-enylbicyclo[4.3.0]nonan-2-one is as follows: 0.68–1.13 ppm (ms, 15H), 1.34–1.63 ppm (m, 5H), 1.77–2.50 ppm (m, 4H), 4.93 ppm (m, 2H), 5.74 ppm (m, 1H).

EXAMPLE 2

Preparation of 7,7,8,9,9-pentamethyl-3-prop-2-enylbicyclo [4.3.0]nonan-2-ol

A mixture of VITRIDE® (Zeeland Chemicals) 70% in toluene, 338 g (1.17 mole) and toluene (732 ml) was heated to 100° C. 7,7,8,9,9-pentamethyl-3-prop-2-enylbicyclo [4.3.0]nonan-2-one, 290 g (1.17 mole) was added over 2 hrs. The excess VITRIDE® was neutralized with 2-propanol (105 g) and the reaction mass was quenched with aqueous sodium hydroxide (280 g of 50% NaOH). The lower aqueous layer was discarded and the organic layer was washed with brine.

The organic layer was distilled to recover toluene, as well as 163 g of 7,7,8,9,9-pentamethyl-3-prop-2-enylbicyclo [4.3.0]nonan-2-ol as a mixture of isomers (Bp 128–130° at 3 mmHg).

The nmr spectrum of 7,7,8,9,9-pentamethyl-3-prop-2-enylbicyclo[4.3.0]nonan-2-ol is as follows: 0–59–1.02 ppm (ms, 15H), 1.14–1.58 ppm (m, 5H), 1.66–2.53 ppm (m, 4H), 3.25–3.87 ppm (dd, 1H), 3.93–4.05 ppm (bs, 1H), 4.98–5.11 ppm (m, 2H), 5.70–5.94 ppm (m, 1H).

EXAMPLE 3

Preparation of 4,10,10,11,12,12-hexamethyl-3-oxatricyclo [7.3.0.0<2,6>]dodecane

A mixture of 7,7,8,9,9-pentamethyl-3-prop-2-enylbicyclo [4.3.0]nonan-2-ol, 163 g (0.65 mole), toluene 163 g and methanesulfonic acid 11.5 g (0.11 mole) was heated to 80–90° C. The reaction mass was aged for 24 hours then cooled to room temperature. The reaction was quenched with 10% aqueous sodium carbonate solution (50 ml). The organic layer was washed twice with 10% aqueous sodium carbonate solution (50 ml) then brine.

The organic layer was distilled to recover toluene as well as 112 g of 4,10,10,11,12,12-hexamethyl-3-oxatricyclo [7.3.0.0<2,6>]dodecane as a mixture of isomers (Bp 95° C. at 2 mm Hg).

The nmr spectrum of 4,10,10,11,12,12-hexamethyl-3-oxatricyclo[7.3.0.0<2,6>]dodecane is as follows: 0.63–0.96 ppm (ms, 18H), 1.0–2.15 ppm (m, 9H), 3.94–4.28 ppm (m, 2H).

EXAMPLE 4

Preparation of 1,1,2,3,3-pentamethyl-5-prop-2-enyl-2,3,5,6, 7-pentahydroinden-4-one A mixture of CASHMERAN® (IFF) 1000 g (4.85 mole), allyl alcohol 1245 g (21.46 mole), and methanesulfonic acid (MSA) 50 g (0.52 mole) was heated to 80–90° C. Volatile organic materials were collected for 24 hrs. The MSA was neutralized 25% sodium methoxide solution in methanol (142 g) and the reaction mass was heated to 180° C. for 5 hours. The mixture was cooled and toluene 1000 milliliters was added. The crude mass was washed twice with brine.

The organic layer was distilled to recover toluene, CASHMERAN® (IFF) (490 g), and 205 g of 1,1,2,3,3-pentamethyl-5-prop-2-enyl-2,3,5,6,7-pentahydroinden-4-one (Bp 139–141° C. at 7 mm Hg).

The nmr spectrum of 1,1,2,3,3-pentamethyl-5-prop-2-enyl-2,3,5,6,7-pentahydroinden-4-one was as follows: 0.87–1.22 ppm (ms, 15H), 1.56–1.78 ppm (m, 2H), 1.99–2.38 ppm (m, 3H), 2.55–2.68 ppm (m, 1H), 5.02–5.11 ppm (m, 2H), 5.72–5.88 ppm (m, 1H).

EXAMPLE 5
Preparation of 5-(allyloxy)-1,1,2,3,3-pentamethyl Indane

The synthesis of the starting material for this example is set forth in U.S. Pat. Nos. 5,227,367, 5,733,866, 5,665,698.

A mixture of 1,1,2,3,3-pentamethyl-4-indanol, 195 g (0.95 mole), methanol (880 ml), sodium iodide, 0.32 g (0.002 mole), and 25% sodium methoxide solution in methanol, 395 g (1.82 mole) was stirred and heated to 40° C. Allyl chloride 151 g (1.96 mole) was added dropwise over 3 hours. The reaction mixture was aged 24 hours at 40° C. The reaction was cooled to room temperature and diluted with 2 liters of water. The pH was adjusted with 100 ml of concentrated hydrochloride acid (37% hydrochloric acid). Toluene (390 ml) was added and the lower aqueous layer was discarded. The organic layer was washed with 300 ml of 10% aqueous sodium carbonate solution then twice with brine.

The organic layer was distilled to recover toluene as well as 122 g of 5-(allyloxy)-1,1,2,3,3-pentamethyl indane (Bp 134–137° C. at 8.7 mm Hg).

The nmr spectrum of 5-(allyloxy)-1,1,2,3,3-pentamethyl indane was as follows: 0.96–1.41 ppm (ms, 15H), 1.83 ppm (q, 1H), 4.49 ppm (dd, 2 H), 5.18–5.42 ppm (m, 2H), 5.95–6.08 ppm (m, 1H), 6.52 ppm (d, 1H), 6.67 ppm (d, 1H), 7.00 ppm (t, 1H).

EXAMPLE 6
Preparation of 1,1,2,3,3-pentamethyl-5-prop-2-enylindan-4-ol 5-(Allyloxy)-1,1,2,3,3-pentamethyl indane, 122 g (0.5 mole) and PRIMOL (Exxon) 36 g was heated to 180–200° C. for 12 hrs.

The reaction mass was distilled providing 38 g of 1,1,2,3,3-pentamethyl-5-prop-2-enylindan-4-ol (Bp 152–154° C. at 5 mmHg).

The nmr spectrum of 1,1,2,3,3-pentamethyl-5-prop-2-enylindan-4-ol was as follows: 0.96–1.42 ppm (ms, 15H), 1.87 ppm (q, 1H), 3.39 ppm (bd, 2H), 5.02 ppm (bs, 1H), 5.16–5.27 ppm (m, 2H), 5.98–6.10 ppm (m, 1H), 6.70 ppm (d, 1H), 6.95 ppm (d, 1H).

EXAMPLE 7
Preparation of 2,6,6,7,8,8-hexamethyl-2,3-dihydroindano[4,5-b]furan A mixture of 1,1,2,3,3-pentamethyl-5-prop-2-enylindan-4-ol 38 g (0.15 mole), toluene 100 ml and p-toluenesulfonic acid (ptsa) 2.3 g (0.01 mole) was heated to 80–90° C. for 15 hours. The reaction mass was cooled to room temperature and quenched with 10% aqueous sodium carbonate (100 ml). The aqueous layer was discarded and organic layer was washed once with brine.

The organic layer was distilled to recover toluene as well as 2,6,6,7,8,8-hexamethyl-2,3-dihydroindano[4,5-b]furan (Bp 124° C. at 4 mm Hg).

The nmr spectrum of 2,6,6,7,8,8-hexamethyl-2,3-dihydroindano[4,5-b]furan was as follows: 1.21–1.68 ppm (ms, 18H), 2.07 ppm (q, 1H), 2.92 ppm (ddd, 1H), 3.41 ppm (ddd, 1H), 5.01–5.16 ppm (m, 1H), 6.75 ppm (d, 1H), 7.07 ppm (d, 1H).

EXAMPLE 8
Preparation of 7,7,8,9,9-pentamethyl-3-(2-methylprop-2-enyl)bicyclo[4.3.0]nonan-2-one Lithium diisopropylamide 1L (2.0 M in THF) was cooled to −10° C. 7,7,8,9,9-pentamethylbicyclo[4.3.0]nonan-2-one, 320 g (1.50 mole) was added dropwise over 2 hrs. The reaction mass was aged 2 hours at room temperature then hexamethylphosporamide available from Aldrich Chemicals, (HMPA), 5.37 g (2 mole %), sodium iodide, 4.50 g (2 mole %) and methallyl chloride, 150 g (1.60 mole) were added over 2 hrs. The reaction mass was heated to reflux for 8 hours. The mixture was cooled to room temperature and quenched with water, 450 g. The aqueous layer was separated then discarded. The organic layer was washed with brine.

The organic layer was distilled to recover THF as well as 384 g of 7,7,8,9,9-pentamethyl-3-(2-methylprop-2-enyl) bicyclo[4.3.0]nonan-2-one(Bp 110° C. at 2 mm Hg).

The nmr spectrum of 7,7,8,9,9-pentamethyl-3-(2-methylprop-2-enyl)bicyclo[4.3.0]nonan-2-one is as follows: 0.68–1.25 ppm (ms, 15H), 1.30–1.87 ppm (m, 6H), 2.03–2.18 ppm (m, 2H), 2.61 ppm (bd, 1H), 4.58–4.73 ppm (m, 2H).

EXAMPLE 9
Preparation of 7,7,8,9,9-pentamethyl-3-(2-methylprop-2-enyl)bicyclo[4.3.0]nonan-2-ol 7,7,8,9,9-Pentamethyl-3-(2-methylprop-2-enyl)bicyclo [4.3.0]nonan-2-one, 140 g (0.53 mole) in toluene (60 g) was fed into RED-AL® (available from Aldrich Chemicals) (65% in toluene) 231 g (0.74 mole) at room temperature over 3 hrs. The reaction mass was quenched with aqueous caustic soda (147 g of 20% NaOH). The mass was heated to 65° C. then water (500 ml) was added. The aqueous layer was separated and extracted once with toluene (86 g). The combined organic layers were dried over sodium sulfate.

The organic layer was distilled to recover toluene as well as 7,7,8,9,9-pentamethyl-3-(2-methylprop-2-enyl)bicyclo [4.3.0]nonan-2-ol as a mixture of isomers (Bp 132–133° C. at 3 mm Hg).

The nmr spectrum of 7,7,8,9,9-pentamethyl-3-(2-methylprop-2-enyl)bicyclo[4.3.0]nonan-2-ol is as follows: 0.61–1.02 ppm (ms, 15H), 1.05–1.56 ppm (m, 6H), 1.71–1.88 ppm (m, 4H), 1.95–2.54 ppm (m, 2H), 3.25–3.96 ppm (m, 1H), 4.67–4.80 ppm (m, 2H).

EXAMPLE 10
Preparation of 4,4,10,10,11,12,12-heptamethyl-3-oxatricyclo [7.3.0.0<2,6>]dodecane A solution of 7,7,8,9,9-pentamethyl-3-(2-methylprop-2-enyl)bicyclo[4.3.0]nonan-2-ol, 2.31 g (8.8 millimole), methanesulfonic acid, 0.04 g (0.4 millimole), and 1-nitropropane 2.31 g was stirred for 24 hrs at room temperature. The reaction mass was neutralized with aqueous sodium carbonate (10% solution). The aqueous layer was separated and discarded. The organic layer was concentrated on a rotary evaporator.

Distillation provided 4,4,10,10,11,12,12-heptamethyl-3-oxatricyclo[7.3.0.0<2,6>]-dodecane as a mixture of isomers (Bp 98° C. at 2 mm Hg).

The nmr spectrum of 4,4,10,10,11,12,12-heptamethyl-3-oxatricyclo[7.3.0.0<2,6>]dodecane was as follows: 0.61–1.27 ppm (ms, 21H), 1.32–1.85 ppm (m, 6H), 2.45–2.61 ppm (m, 1H) 3.92–3.98 ppm (m, 1H).

EXAMPLE 11
Preparation of 1,1,2,3,3-pentamethyl-5-(2-methylprop-2-enyl)-2,3,5,6,7-pentahydroinden-4-one A solution of CASHMERAN® (IFF) 400 g (1.94 mole) and THF (200 milliliter) was fed into lithium diisopropylamide 1L (2.0 M in THF) at −10° C. The reaction mass was aged for 2 hours and allowed to warm to 0° C. Methallyl chloride 248 g (2.7 mole) was added over 2 hours. The reaction was warmed to room temperature, then heated to 60° C. for 20 hours. The mixture was cooled and quenched with 10% hydrochloric acid (1 liter). The crude mass was washed with brine.

The organic layer was distilled to recover THF and 310 g of 1,1,2,3,3-pentamethyl-5-(2-methylprop-2-enyl)-2,3,5,6,7-pentahydroinden-4-one (Bp 142–143° C. at 2 mm Hg).

The nmr spectrum of 1,1,2,3,3-pentamethyl-5-(2-methylprop-2-enyl)-2,3,5,6,7-pentahydroinden-4-one is as follows: 0.86–1.23 ppm (ms, 15H), 1.36–1.66 ppm (m, 2H), 1.72 ppm (bs, 3H), 1.75–2.39 ppm (m, 4H), 2.59–2.71 ppm (m, 1H), 4.70 ppm (d, 2H).

EXAMPLE 12
Preparation of 3-(2-bromoethyl)-7,7,8,9,9-pentamethylbicyclo[4.3.0]nonan-2-one A solution of 7,7,8,9,9-pentamethylbicyclo[4.3.0]nonan-2-one 200 g (0.97 mole) and THF (100 mL) is fed into lithium diisopropylamide 1L (1.0 M in THF) and HMPA (10 g 5 mole percent) at −30° C. The reaction mass is aged for 2 hours and allowed to warm to 0° C. 1,2-Dibromoethane 200 g (1.06 mole) is added over 2 hours. The reaction is warmed to room temperature and aged for 24 hrs. The mixture is quenched with 10% hydrochloric acid (200 mL). The crude mass is washed with brine.

Distillation would provide 3-(2-bromoethyl)-7,7,8,9,9-pentamethylbicyclo[4.3.0]nonan-2-one as a mixture of isomers.

EXAMPLE 13
Preparation of 3-(2-bromoethyl)-7,7,8,9,9-pentamethylbicyclo[4.3.0]nonan-2-ol A solution of 3-(2-bromoethyl)-7,7,8,9,9-pentamethylbicyclo[4.3.0]nonan-2-one, 200 g (0.63 mole) in toluene (60 g) is fed into RED-AL® (65% in toluene) 218 g (0.70 mole) at 60° C. in 1 hr. The reaction mass is quenched with aqueous caustic soda (200 g of 50% NaOH) at 60° C. The mass is diluted with water (500 ml) and cooled to room temperature. The aqueous layer is separated and discarded.

Distillation would provide 3-(2-bromoethyl)-7,7,8,9,9-pentamethylbicyclo[4.3.0]nonan-2-ol as a mixture of isomers.

EXAMPLE 14
Preparation of 10,10,11,12,12-pentamethyl-3-oxatricyclo[7.3.0.0<2,6>]dodecane A solution of 3-(2-bromoethyl)-7,7,8,9,9-pentamethylbicyclo[4.3.0]nonan-2-ol, 50 g (0.16 mole) and THF (100 ml) is fed into sodium hydride 6.4 g (60% dispersion in mineral oil) and THF (300 ml) at room temperature. The reaction mass is heated to reflux for 8 hours and cooled to room temperature. The reaction mass is quenched with brine (100 ml). The aqueous layer is separated and discarded.

Distillation would provide 10,10,11,12,12-pentamethyl-3-oxatricyclo[7.3.0.0<2,6>]-dodecane as a mixture of isomers.

EXAMPLE 15

A fragrance was prepared according to the following formulation:

| Materials | Parts |
|---|---|
| 4,10,10,11,12,12-hexamethyl-3-oxatricyclo[7.3.0.0<2,6>]dodecane | 1 |
| BORNAFIX ® (IFF) | 3 |
| CEDRAFIX ® (IFF) | 2.5 |

| Materials | Parts |
|---|---|
| CELESTOLIDE ® (IFF) | 4 |
| CITRALVA ® (IFF) | 1 |
| Citrus oil distilled | 12 |
| CYCLACET ® (IFF) | 3 |
| CYCLOGALBANIFF ® (IFF) | 1 |
| Dihydro Myrcenol | 40 |
| FLEURANIL ® (IFF) | 1 |
| Geranium Bourbon Oliffac | 0.5 |
| Hexyl Cinnamic Aldehyde | 4.5 |
| ISO E SUPER ® (IFF) | 2.5 |
| KHARISMAL ® (IFF) | 2 |
| KOAVONE ® (IFF) | 1.5 |
| Linalyl Acetate | 5 |
| PHENOXANOL ® (IFF) | 3 |
| PRECYCLEMONE B ® (IFF) | 1.5 |
| Pseudo Linalyl Acetate | 5 |
| Styralyl Acetate | 1 |
| VIGOFLOR ® | 1 |
| ZENOLIDE ® (IFF) | 4 |

This fragrance was described as having a citrus odor.

EXAMPLE 16

The following materials made in the above examples were described as having the following fragrance characteristics:

| Material | Odor |
|---|---|
| 4,10,10,11,12,12-hexamethyl-3-oxatricyclo[7.3.0.0<2,6>]dodecane | Amber, Woody |
| 4,4,10,10,11,12,12-heptamethyl-3-oxatricyclo[7.3.0.0<2,6>]dodecane | Amber, Woody |
| 1,1,2,3,3-pentamethyl-5-prop-2-enyl-2,3,5,6,7-pentahydroinden-4-one | Sweet, Musky, Fruity |
| 1,1,2,3,3-pentamethyl-5-(2-methylprop-2-enyl)-2,3,5,6,7-pentahydroinden-4-one | Sweet, Raspberry, Musky |

What is claimed is:

1. The compound according to the structure:

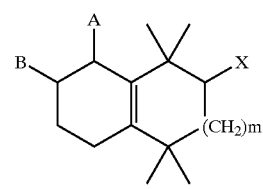

where A is

B is

or A and B together form the ring structure and X, R' and R are independently H and $CH_3$ and m=0 or 1.

2. The compound of claim 1 which is incorporated into a fragrance formulation.

3. A method for improving, enhancing or modifying the odor properties of a fragrance by incorporating an olfactory acceptable amount of the compound of claim 1.

4. The method of claim 3 wherein the fragrance is incorporated into a product selected from perfumes, colognes, toilet waters, personal care products, cleaning products and air fresheners.

5. The method of claim 4 wherein the cleaning product is selected from the group consisting of detergents, dishwashing compositions, scrubbing compounds and window cleaners.

6. The method of claim 4 wherein the product is a personal care product.

7. The compound of claim 1 with the structure:

where A is

B is

R is independently H and $CH_3$ and X is $CH_3$.

8. The compound of claim 1 wherein A and B together form a ring structure to provide a compound with the structure:

where X is $CH_3$ R and R' are independently H and $CH_3$ and m=0.

9. A method for improving, enhancing or modifying the odor properties of a fragrance by incorporating an olfactory acceptable amount of the compound of claim 8.

10. The method of claim 9 wherein the compound is selected from the group consisting of 4,10,10,11,12,12-hexamethyl-3-oxatricyclo[7.3.0.0<2,6>]dodecane, 4,4,10,10,11,12,12-heptamethyl-3-oxatricyclol[7.3.0.0<2,6>]dodecane, 1,1,2,3,3-pentamethyl-5-prop-2-enyl-2,3,5,6,7-pentahydroinden-4-one and 1,1,2,3,3-pentamethyl-5-prop-2-enyl-2,3,5,6,7-pentahydroinden-4-one.

11. The compound 4,10,10,11,12,12-hexamethyl-3-oxatricyclo[7.3.0.0<2,6>]dodecane of claim 10 having any of the following isomeric configurations:

(1R, 2R, 4R, 6R, 9R, 11R)-Z, (1S, 2S, 4R, 6R, 9S, 11S)-Z, (1S, 2R, 4R, 6R, 9S, 11S)-Z, (1R, 2R, 4R, 6R, 9R, 11S)-Z, (1R, 2S, 4R, 6S, 9R, 11S)-Z, (1R, 2R, 4R, 6S, 9S, 11S)-Z, (1R, 2R, 4R, 6R, 9S, 11R)-Z, (1S, 2S, 4S, 6R, 9S, 11R)-Z, (1S, 2R, 4R, 6R, 9R, 11s)-Z, (1R, 2R, 4R, 6S, 9R, 11R)-Z, (1S, 2S, 4R, 6S, 9R, 11S)-Z, (1S, 2S, 4S, 6S, 9S, 11S)-Z, (1R, 2R, 4S, 6R, 9R, 11R)-Z, (1S, 2R, 4S, 6R, 9S, 11S)-Z, (1S, 2R, 4S, 6S, 9R, 11S)-Z, (1R, 2S, 4R, 6R, 9R, 11R)-Z, (1R, 2S, 4R, 6S, 9S, 11S)-Z, (1S, 2S, 4R, 6R, 9R, 11S)-Z, (1S, 2R, 4R, 6R, 9R, 11R)-Z, (1s, 2S, 4R, 6R, 9S, 11R)-Z, (1S, 2S, 4S, 6R, 9R, 11R)-Z, (1R, 2R, 4R, 6R, 9S, 11S)-Z, (1S, 2R, 4R, 6S, 9S, 11R)-Z, (1S, 2S, 4R, 6S, 9S, 11R)-Z, (1R, 2R, 4R, 6S, 9S, 11R)-Z, (1S, 2R, 4R, 6S, 9R, 11S)-Z, (1R, 2R, 4S, 6S, 9S, 11S)-Z, (1R, 2R, 4S, 6S, 9R, 11R)-Z, (1R, 2R, 4S, 6R, 9S, 11R)-Z, (1S, 2R, 4S, 6R, 9S, 11S)-Z, (1R, 2S, 4S, 6R, 9R, 11R)-Z, (1R, 2R, 4S, 6S, 9R, 11S)-Z, (1S, 2S, 4S, 6S, 9R, 11S)-Z, (1S, 2S, 4R, 6R, 9R, 11R)-Z, (1R, 2S, 4R, 6R, 9S, 11R)-Z, (1S, 2S, 4R, 6R, 9S, 11R)-Z, (1R, 2R, 4R, 6S, 9S, 11S)-Z, (1R, 2S, 4R, 6R, 9S, 11S)-Z, (1S, 2R, 4R, 6S, 9S, 11S)-Z, (1R, 2R, 4S, 6S, 9S, 11R)-Z, (1R, 2S, 4S, 6R, 9S, 11S)-Z, (1S, 2S, 4R, 6R, 9S, 11S)-Z, (1R, 2S, 4S, 6S, 9R, 11R)-Z, (1R, 2S, 4S, 6R, 9R, 11S)-Z, (1S, 2S, 4S, 6R, 9R, 11S)-Z, (1S, 2S, 4S, 6R, 9R, 11R)-Z, (1R, 2R, 4S, 6S, 9R, 11R)-Z, (1S, 2S, 4S, 6S, 9R, 11R)-Z, (1R, 2S, 4S, 6S, 9S, 11R)-Z, (1S, 2R, 4S, 6R, 9S, 11R)-Z, (1R, 2S, 4S, 6S, 9S, 11S)-Z, (1R, 2R, 4R, 6S, 9R, 11S)-Z, (1S, 2S, 4S, 6S, 9S; 11R)-Z, (1S, 2S, 4R, 6S, 9R, 11R)-Z, (1R, 2R, 4S, 6R, 9S, 11S)-Z, (1S, 2S, 4S, 6S, 9R, 11S)-Z, (1R, 2S, 4S, 6R, 9S, 11R)-Z, (1R, 2S, 4R, 6S, 9R, 11R)-Z, (1S, 2S, 4S, 6R, 9S, 11S)-Z, (1R, 2S, 4S, 6R, 9R, 11S)-Z, (1S, 2R, 4S, 6R, 9R, 11R)-Z, (1S, 2S, 4R, 6S, 9S, 11S)-Z, (1S, 2R, 4S, 6S, 9S, 11S)-Z, or (1R, 2R, 4S, 6S, 9R, 11S)-Z.

12. The method of claim 3 wherein the olfactory acceptable amount of claim 1 is from about 0.005 to about 10 weight percent of the fragrance.

13. The method of claim 12 wherein the olfactory acceptable amount is from about 0.5 to about 8 weight percent.

14. A fragrance formulation containing from about 0.005 to about 10 weight percent of the compound of claim 7.

15. A fragrance formulation containing from about 0.005 to about 10 weight percent of the compound of claim 8.

16. The fragrance formulation of claim 14 incorporated into a product selected from perfumes, colognes, toilet waters, personal care products, cleaning products and air fresheners.

17. The fragrance formulation of claim 15 incorporated into a product selected from perfumes, colognes, toilet waters, personal care products, cleaning products and air fresheners.

* * * * *